(12) United States Patent
Mun et al.

(10) Patent No.: US 6,857,778 B2
(45) Date of Patent: *Feb. 22, 2005

(54) SURGICAL SCANNING SYSTEM AND PROCESS FOR USE THEREOF

(76) Inventors: Inki Mun, 1 Apple Ct., Nanuet, NY (US) 10954; Allen B. Kantrowitz, 7980 Biscayne Point Cir., Miami Beach, FL (US) 33141

( * ) Notice: Subject to any disclaimer, the term of this patent is extended or adjusted under 35 U.S.C. 154(b) by 0 days.

This patent is subject to a terminal disclaimer.

(21) Appl. No.: 10/226,276

(22) Filed: Aug. 22, 2002

(65) Prior Publication Data

US 2002/0196906 A1 Dec. 26, 2002

Related U.S. Application Data

(63) Continuation of application No. 09/620,161, filed on Jul. 20, 2000, now Pat. No. 6,456,684.
(60) Provisional application No. 60/145,349, filed on Jul. 23, 1999.

(51) Int. Cl.[7] .................................................. A61B 6/08
(52) U.S. Cl. ......................... 378/206; 378/20; 378/209; 5/601
(58) Field of Search .............................. 128/849; 378/4, 378/15, 20, 65, 196, 197, 198, 206, 209; 356/154, 399, 614, 615, 616; 5/601, 600, 611; 600/415; 606/130

(56) References Cited

U.S. PATENT DOCUMENTS

| 2,872,259 A | 2/1959 | Thorpe ........................... 5/613 |
|---|---|---|
| 3,428,307 A | 2/1969 | Hunter et al. .................. 5/601 |
| 3,766,384 A | 10/1973 | Anderson .................... 378/209 |
| 4,145,612 A | 3/1979 | Cooper ........................ 378/208 |
| 4,233,507 A | 11/1980 | Volz ............................. 378/18 |
| 4,333,638 A | 6/1982 | Gillotti .......................... 5/613 |
| 4,506,872 A | 3/1985 | Westerberg et al. ........... 5/601 |
| 4,568,071 A | 2/1986 | Rice ............................... 5/601 |
| 4,584,731 A | 4/1986 | Carter ............................ 5/632 |
| 4,592,352 A | * 6/1986 | Patil ........................... 606/130 |
| 4,613,122 A | 9/1986 | Manabe ......................... 5/601 |
| 4,616,814 A | 10/1986 | Harwood-Nash et al. ...... 5/601 |
| 4,645,933 A | 2/1987 | Gambini et al. ......... 250/363 S |
| 4,706,665 A | 11/1987 | Gouda ......................... 606/130 |
| 4,727,328 A | 2/1988 | Carper et al. ............... 324/318 |
| 4,860,331 A | * 8/1989 | Williams et al. ............ 378/163 |
| 4,910,819 A | 3/1990 | Brown .......................... 5/484 |
| 4,914,682 A | 4/1990 | Blumenthal .................. 378/20 |
| 4,928,283 A | 5/1990 | Gordon ........................ 378/20 |

(List continued on next page.)

FOREIGN PATENT DOCUMENTS

| WO | WO 99/11176 | 3/1999 | ............ A61B/6/04 |

*Primary Examiner*—Edward J. Glick
*Assistant Examiner*—Courtney Thomas
(74) *Attorney, Agent, or Firm*—Gifford, Krass, Groh, Sprinkle, Anderson & Citkowski, P.C.

(57) ABSTRACT

A surgical scanning system includes a scanner supported on a carrier movable relative to an operating room table. The carrier engages a guide that is collinear with the long axis of an operating room table. The relative movement between an operating room table and a scanner along a guide decreases the likelihood of collision therebetween. The ability to collect a scan of a patient while on an operating room table increases the likelihood of a successful surgical outcome.

26 Claims, 2 Drawing Sheets

U.S. PATENT DOCUMENTS

| | | | | |
|---|---|---|---|---|
| 4,941,164 A | | 7/1990 | Schuller et al. | 378/205 |
| 4,942,597 A | * | 7/1990 | Van Acker et al. | 378/197 |
| 4,944,501 A | | 7/1990 | Sireul et al. | 5/601 |
| 4,984,774 A | | 1/1991 | Zupancic et al. | 5/601 |
| 5,020,089 A | * | 5/1991 | Cramer et al. | 378/196 |
| 5,034,969 A | | 7/1991 | Ozaki | 378/18 |
| 5,097,132 A | | 3/1992 | Plummer | 250/363.08 |
| 5,177,823 A | | 1/1993 | Riach | 5/636 |
| 5,178,146 A | | 1/1993 | Giese | 128/653.2 |
| 5,229,102 A | | 7/1993 | Minet et al. | 423/652 |
| 5,259,011 A | | 11/1993 | Petro | 378/4 |
| 5,276,927 A | | 1/1994 | Day | 5/622 |
| 5,335,384 A | | 8/1994 | Foster et al. | 5/622 |
| 5,347,668 A | | 9/1994 | Manning | 5/622 |
| 5,369,679 A | * | 11/1994 | Sliski et al. | 378/65 |
| 5,448,607 A | | 9/1995 | McKenna | 378/4 |
| 5,475,884 A | | 12/1995 | Kirmse et al. | 5/601 |
| 5,499,415 A | | 3/1996 | McKenna | 5/601 |
| 5,525,322 A | | 6/1996 | Willms | 423/653 |
| 5,560,728 A | | 10/1996 | McFadden | 403/53 |
| 5,564,662 A | | 10/1996 | Lüssi et al. | 248/188.2 |
| 5,638,419 A | | 6/1997 | Ingwersen | 378/4 |
| 5,644,616 A | * | 7/1997 | Landi et al. | 378/206 |
| 5,657,368 A | | 8/1997 | Röckseisen | 378/206 |
| 5,661,859 A | | 9/1997 | Schaefer | 5/621 |
| 5,675,625 A | | 10/1997 | Röckseisen | 378/206 |
| 5,675,851 A | | 10/1997 | Feathers | 5/632 |
| 5,740,222 A | | 4/1998 | Fujita et al. | 378/4 |
| 5,754,997 A | * | 5/1998 | Lüssi et al. | 5/618 |
| 5,758,374 A | | 6/1998 | Ronci | 5/507.1 |
| 5,802,719 A | | 9/1998 | O'Farrell, Jr. et al. | 29/897.35 |
| 5,875,780 A | * | 3/1999 | Rodriguez | 128/849 |
| 5,997,176 A | | 12/1999 | Fairleigh | 378/196 |
| 6,003,174 A | | 12/1999 | Kantrowitz et al. | 5/601 |
| 6,105,578 A | * | 8/2000 | Sommers et al. | 128/849 |
| 6,155,713 A | * | 12/2000 | Watanabe | 378/197 |
| 6,199,233 B1 | | 3/2001 | Kantrowitz et al. | 5/601 |
| 6,203,196 B1 | * | 3/2001 | Meyer et al. | 378/197 |
| 6,212,251 B1 | | 4/2001 | Tomura et al. | 378/15 |
| 6,241,670 B1 | * | 6/2001 | Nambu | 600/427 |
| 6,256,528 B1 | | 7/2001 | Zonneveld et al. | 600/425 |
| 6,289,073 B1 | | 9/2001 | Sasaki et al. | 378/4 |
| 6,322,251 B1 | | 11/2001 | Ballhaus et al. | 378/209 |
| 6,423,077 B2 | * | 7/2002 | Carol et al. | 606/130 |
| 6,456,684 B1 | * | 9/2002 | Mun et al. | 378/20 |

* cited by examiner

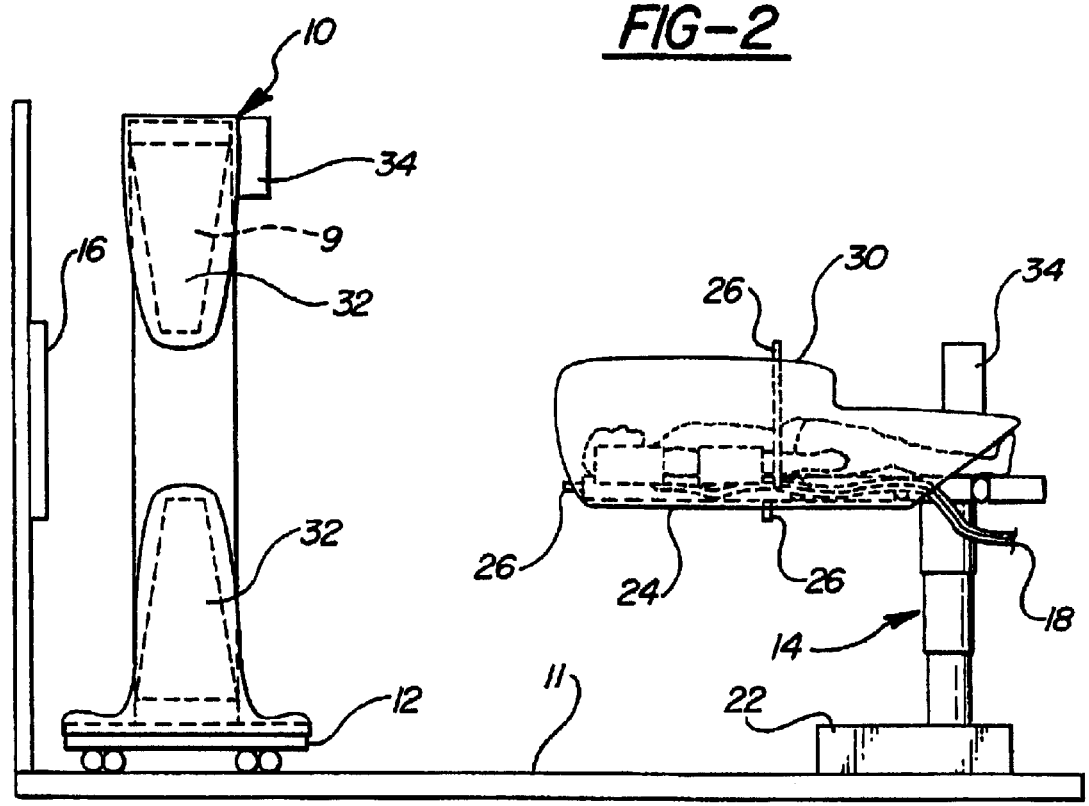

SURGICAL SCANNING SYSTEM AND PROCESS FOR USE THEREOF

RELATED APPLICATIONS

This application is a continuation of U.S. patent application Ser. No. 09/620,161 filed Jul. 20, 2000, U.S. Pat. No. 6,456,684 B1, which claims priority of U.S. Provisional Patent Application Serial No. 60/145,349 filed Jul. 23, 1999, and are incorporated herein by reference.

FIELD OF THE INVENTION

The present invention relates to a surgical scanning system and more particularly to a scanning system selectively positionable about a surgical table.

BACKGROUND OF THE INVENTION

Computerized tomography (CT) has developed as a powerful diagnostic tool affording a surgeon detailed imagery as to the location of abnormal tissue intended to be incised. CT scanning is typically performed as a diagnostic in response to clinical manifestations of disease such as neurological disorders. CT scanning is also used in the context of pre- and post-surgical evaluations to assess the location and size of an abnormal tissue mass, and the success of the abnormal tissue mass incision, respectively. When post-surgical CT scanning is performed during surgical recovery, the discovery of a residual abnormal tissue mass requires the scheduling of an additional surgical procedure. With current conventional procedures and equipment, CT scanning performed while a patient is still under surgical anesthesia requires the transport of the patient to a CT scanning facility thereby compromising surgical field sterility and risking injury to the anesthetized patient.

As CT scanning allows for earlier diagnosis and more complete assessment as to an abnormal tissue mass, a physician is better able to assess a favorable outcome for a surgical intervention as compared to radiation or chemo-therapeutic treatments. While irregularly shaped, deeply situated or multiple abnormal tissue masses were previously likely to be deemed inoperable, technological advances involving position sensing surgical aids such as catheters and robotically controlled surgical instruments will increasingly allow for successful complex surgical interventions. The usage of position sensing surgical instruments requires a reference frame within the patient's body relative to the fixed components of the surgical aid. Once a frame of reference exists, a catheter or other position sensing surgical aid is free to navigate a preselected pathway to a desired location within the body of a patient, thereby allowing access to body tissues which would otherwise not be accessible through line of sight manual surgical techniques.

Owing to the limitations in current applications of CT scanning, there exists a need for CT scanning to be performed while an anesthetized surgical patient lies on an operating table. Such a CT scanning system affords a surgeon instant feedback as to the success of abnormal tissue excision and with less likelihood of surgical field contamination. Further, such a system would provide a standard frame of reference between a body tissue and position sensing surgical aids.

SUMMARY OF THE INVENTION

A surgical scanning system includes an operating room table having a long axis, a scanner supported on a carrier and a guide adapted to engage the carrier. The carrier being movable relative to the operating room table along the guide. The long axis of the operating room table being collinear with the guide.

An improvement to a wheeled medical scanner including a scanner mounted on a wheeled platform adapted to encompass an operating room table portion along a long axis of the operating room table is disclosed. The improvement to the wheeled medical scanner includes a guide roller attached to the wheeled platform of the scanner such that the guide roller is adapted to engage a mechanical guide affixed to the operating room floor collinear with the long axis of the operating room table.

With the ability to move a medical scanner relative to an operating room table, a method becomes available for performing a medical scan during a surgical procedure. The process including identifying a scan region proximal to a long axis of an operating room table. Thereafter, moving a scanner along a linear guide collinear with the long axis of the operating table so as to encompass the scan region. A scan of the scan region is then collected. The scanner is then retracted along the guide to a location remote from the operating room table, thereby allowing surgical personnel access to the operating field.

BRIEF DESCRIPTION OF THE DRAWINGS

FIG. 2 is a partial cutaway side view of the embodiment shown in FIG. 1 with drapes in position.

DETAILED DESCRIPTION OF THE PREFERRED EMBODIMENTS

Figure 1:
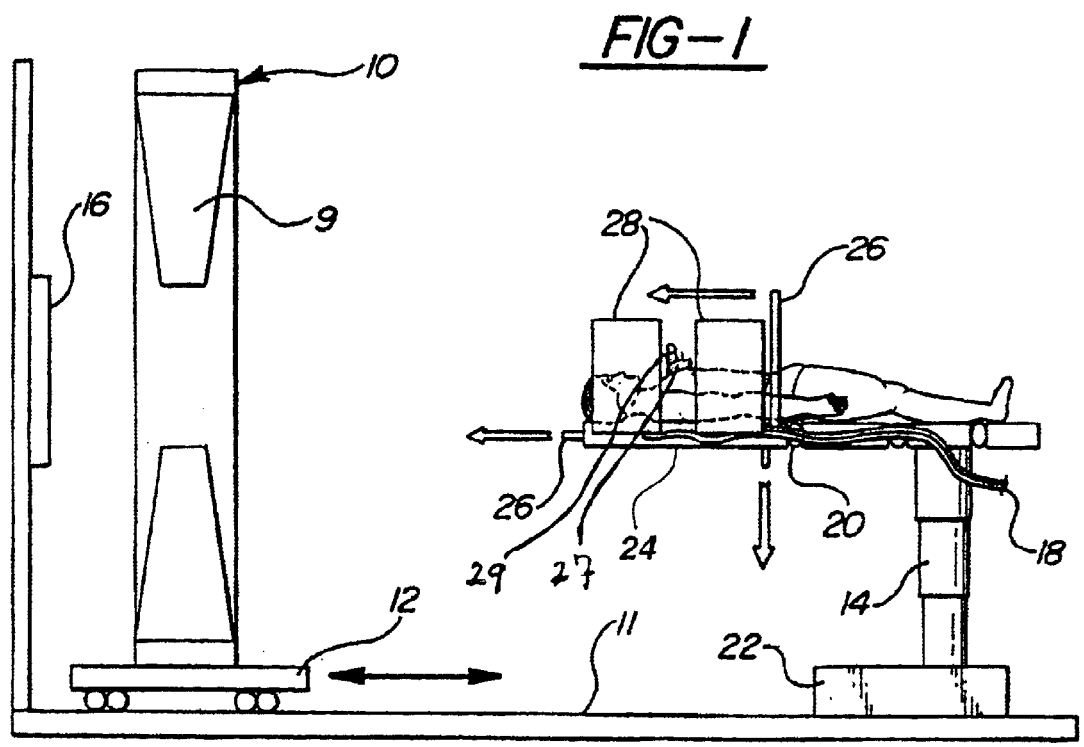
FIG. 1 is a side view of a surgical scanning system according to one embodiment of the present invention.

"CT gantry" as used herein refers to those structures within a CT scan ring capable of obtaining cross axial transmission information from any of 360° of the projection across the central bore of the CT scanner.

The present invention has utility in obtaining computerized tomography (CT) images during the conduct of a surgical procedure on a patient. The present invention directly addresses patient safety issues by minimizing the chances of collision between a moving CT gantry, the patient and associated surgical equipment.

CT movement is constrained herein along a predefined guide collinear with the long axis of the CT compatible operating room (OR) table. When not active, the CT gantry is moved in a precise manner along the axis of the patient to the distance sufficient to allow conventional unimpeded access to the patient by OR personnel.

The movement of the CT gantry is constrained by a mobile carrier illustratively including a platform, pallet or dolly. This mobile carrier moves the CT gantry in a controlled fashion along a guideway. An OR table is positioned collinear with the axis of movement of the CT gantry and carrier system. Movement of the carrier is guided by manual, mechanical, electronic, or optical systems.

The "CT compatible OR table" of the present invention is characterized as a patient support table which allows a patient to be safely positioned for a surgical procedure and which has structural design characteristics which permit CT images to be obtained during surgery. The table is optionally movable. Prior to CT scanning, the table is positioned on the floor allowing safe scanning of the patient.

Movement of a CT gantry of the present invention is constrained along a predefined guide collinear with the long axis of a CT compatible OR table. The CT gantry is mounted on a mobile pallet. This pallet moves the CT gantry and carrier system 10 in a controlled fashion along a line dictated by a guide. Preferably, the guide track is linear.

In another embodiment, a conventional wheeled pallet CT scanner designed to encompass an OR table portion is adapted with retractable guide rollers, the guide rollers adapted to engage a mechanical guide installed in the OR collinear with the long axis of an OR table. It is appreciated that the mechanical guide is installed in either a temporary or permanent basis.

In still another embodiment, a ceiling or wall mounted track and dolly system allows a single CT scanner to be shared between a plurality of operating rooms. The track and dolly system operating as described herein with regard to a floor mounted guide system.

The CT compatible OR table allows a patient to be safely and properly positioned for a cranial, spinal, or other surgical procedure. The table has design characteristics which permit CT images to be obtained during surgery.

Specialized surgical drapes and patient protection systems are also provided with the surgical scanning system of the present invention.

While the present invention is detailed herein with reference to a CT scanner, it is appreciated that the present invention readily incorporates other instruments illustratively including x-ray, magnetic resonance imaging and ultrasound.

In reference to FIG. 1, a CT gantry and carrier system 10 is selectively positioned along a temporary or permanent guideway 11 which is installed in the OR. The guideway 11 is an alignment aid used to control the movement of a CT carrier 12. The guide 11 provides positional information to aid in the accurate positioning of a CT compatible OR table 14 and of a distant alignment target device 16. If the guide is mounted on the floor, it optionally also provides a surface to facilitate movement of the CT carrier 12 and of the OR table 14. The guide 11 is preferably fabricated in sections to ease initial on-site delivery and installation. The guide surface finish or a replaceable cover thereof is compatible with standard OR requirements for cleaning purposes.

A CT gantry 9 rests on the movable carrier 12, together making up gantry and carrier system 10. The transport of the carrier 12 moves the CT gantry 9 from its initial disengaged position, which allows normal unfettered access to a patient on the OR table 14, to the scan position over a patient on the OR table 14. The carrier 12 engages the guide 11 in a manner which assures the axis of movement of the CT 10 is collinear with the axis of the guide 11 and, therefore, with the OR table 14. The carrier movement may be motorized or non-motorized.

The OR table 14 has controls to allow the patient support surface to be accurately leveled as well as positioned as needed for a surgical procedure. The OR table 14 accepts ancillary tubing and monitoring lines 18. The OR table 14 optionally includes at least one articulation 20 to promote positional adjustments. A patient is safely supported beyond the footprint of the table base 22.

The CT compatible extension 24 supports a patient while allowing radiolucent imaging in 360 degrees transverse to the long axis of the OR table 14. The table extension 24 is fabricated from carbon fiber/graphite composite or other radiolucent materials. Optionally, embedded within the extension 24 or attached thereto are specialized markers of contrasting radiodensity which allow accurate positional information to be encoded in CT images obtained herein. The table extension 24 is optionally engineered to engage fittings on specialized surgical drapes and rigid patient protection devices described hereinbelow. Preferably, the table extension edges are engineered to engage fittings.

A distant alignment target device 16 is used in conjunction with an alignment device 26. The alignment device 26 is used in conjunction with a laser mounted on the OR table 14 or table extension 24. The device 26 is secured to the table either directly or indirectly through drapes as detailed hereinbelow. Use of the target device 16 ensures that the axis of the OR table 14 and table extension 24 have been accurately aligned co-axially with the axis of the CT guide 11. It is appreciated that the relative positions of target device 16 and alignment device 26 can be transposed. Thus positioned, collision between the CT system 10 and the table extension 24 is prevented.

It is appreciated that alternate alignment configurations and methods are operative within the present invention including photodetectors, acoustic sensors and referencing fixtures secured within the OR at locations remote from the OR table. Thus, the origin of frame of reference is arbitrary and mathematically can be transferred anywhere within the OR.

An alignment device allows a physician to measure an angle subtended between a medical instrument and a reference platform or an OR table. A reference platform 27 is temporarily secured to a surgical patient. The reference platform is constructed of an x-ray and/or magnetic resonance compatible, temporary structural material illustratively including plastics such as TEFLON and HDPE; low Z metals such as aluminum; and cartilaginous materials. The platform straddles the surgical site and is secured to the patient via small screws, posts, clamps or pads. The attachment points are optionally permanently mounted on the reference platform or are selectively detachable. Optionally, irregularities are incorporated into the surfaces or edges of the reference frame to form the basis of position and unique identification information as is determined by medical imaging equipment.

A trajectory measurement device 29 is optionally secured to the reference platform during surgery. The device geometry allows it to securely engage the reference frame mounted to the patient. The trajectory measuring device allows the physician to pass the medical instrument to the entry point. As the physician holds the medical instrument at the entry point and later as he advances the medical instrument past the entry point further into the body, the trajectory measuring device measures two angles between the axis of the medical instrument and the reference frame. These two angle measurements can be passed to a display system via electronic, optical, or other means. The display system presents the information to the physician in a clinically meaningful fashion. The display system may use a computer to present medical image information superimposed upon the trajectory information. Optionally, the system is capable of calculating the depth of the instrument.

One method that the trajectory measuring device is used to measure the angle of the axis of the medical instrument would be as follows: a planar imaging device is incorporated into each of two walls of the central clear channel. Opposite each planar imaging device is fixed with a planar light source. The light sources and imaging devices may be fitted with polarizing filters to improve signal to noise ratio. As the medical instrument is passed through the central clear channel, each imaging device will detect one view of the instrument by changes in the image. This information is passed to information processing equipment by electric, optical, magnetic, or other means. A second method of measuring the angles would be achieved by substitution of the planar arrays with multiple linear arrays of detectors and sources or by multiple pointlike detectors and sources. Other methods to measure the angle of the medical instrument within the central clear channel would be based on magnetic, electromagnetic, acoustic or mechanical principles.

The system is designed to allow the trajectory measuring device to be placed successively on each of several reference frames which had already been secured to the patient. This is of importance when the patient may require use of the system to address clinical needs such as biopsy at each of several locations. Optionally, the trajectory measuring device has embedded systems which allow the device to sense which of the several reference frames to which it is attached. In sensing these irregularities, the system can detect secure seating of the trajectory measuring device on the reference frame. Optionally, the trajectory sensing device can confirm secure seating on the reference frames. This additional information can be passed from the reference frame, via the properly seated trajectory device, to the information processing system. This information may be used to simplify the overall use protocols of the surgical scanning system of the present invention.

Optionally, additional patient safety is provided by a selectively retractable and/or removable shield 28, which is secured to the table extension 24. The shield 28 serves to limit patient exposure to the CT gantry 9 in cases in which patients have some residual or unintended movement. Provision is made to ease the task of maintaining sterility during retraction and deployment of the shields.

A shield of the present invention is formed as a rigid article designed to protect surgical patient regions such as the head, neck, and other extremities from physical contact with a CT gantry. Further, a shield also promotes surgical field sterility when used adjacent thereto. A shield is formed to nearly any shape provided the size and shape adequately cover a desired region of a surgical patient. Illustrative shapes include a dome, bucket and cylinder. Preferably, the shield is optically transparent, else one or more optically transparent viewing windows are incorporated therein. More preferably, the shield is also x-ray transparent. A shield according to the present invention is optionally secured to the operating room table. Securing means illustratively include a bow, three point fixation, dovetail clamp, interlocking grooves and the like.

A shield is used to check whether a bundled surgical patient will fit within the bore of a CT gantry. Optionally, the shield is segmented such that portions thereof are removable.

To promote aseptic conditions in the operating field, specialized surgical drapes are optionally provided which serve to maintain sterility of the surgical field as the CT gantry 9 moves over a patient as shown in FIG. 2. Drapes 30 and 32 are preferably placed on both the OR table patient volume and over CT system, respectively. Adhesive or mechanical fixturing means are integrated into the drape material to secure the drapes 30 to the underlying OR table 14 and CT system 10. Additionally, at least one fixturing fitting is optionally integrated into the drapes 30 to secure external medical equipment (not shown) to the drape 30 or, indirectly, to the OR table 14 or CT gantry 10.

The surgical drape 30 is provided herein to maintain an aseptic surgical field both above and below a patient supported upon a surgical table. While it is appreciated that numerous configurations of drapes can be created to surround a patient above and below a supporting table, preferably a tube-type drape encompasses a patient supported on a table. Employing similar surgical drapes about medical equipment, such equipment is safely and repeatedly placed around the surgical field without contaminating the surgical field or the medical equipment. Both open and closed tube drapes are operative herein.

According to one method of the present invention, a drape is collapsed along its long axis which preferably has a fold facilitating regular and compact disengagement, such fold illustratively including an accordion fold. Rigid or semi-rigid structures incorporated with a drape operate as hand holds such that sterile gowned personnel selectively expand and collapse the drape along the length of the patient. Preferably, the mechanical structures are formed as ring handles. Ring handles optionally engage fixtures on the operating room table or are selectively removable.

An alternative method of utilizing a drape according to the present invention entails collapsing a drape to the edge of a surgical table. A drawstring or other means is optionally incorporated into the drape to gather the drape together to more closely conform to surgical table and patient contours.

A fixture is optionally bonded to the exterior surface of a drape. A fixture is optionally included to engage complementary fixtures on the operating room table. A similar fixture on the internal surface of the drape permits complementary fixtures to be secured thereto. Thus, sterile equipment is securely fastened to the operating room table through the drape without destroying the sterile integrity of the mechanical drape barrier. Other types of incorporated fixtures facilitate placement and attachment of medical equipment, tubing, wires and the like. A drape according to the present invention is optionally provided with a preformed opening in the drape. The drape opening is positioned in the vicinity of the surgical incision upon extension of the drape over a patient supported on an operating room table.

The specialized drape 32 is provided herein to allow a CT scan device to be used during a sterile procedure. The drape 32 permits the CT scanner to encompass a patient without violating the sterile field. The CT drape 32 optionally incorporates several fixtures bonded to the drape. Fixtures on the non-sterile side of the drape engage complementary fixtures on the CT scanner, whereas fixtures on the sterile side of the drape permit complementary fixtures to be secured to the drape and by way of the incorporated drape fixture to the CT scanner. Thus, sterile equipment is attached to the CT through the drape without destroying the integrity of the sterile mechanical barrier. It is appreciated that other types of fixtures are incorporated to one side of the drape in order to place and secure medical equipment, tubing, wires and the like.

A similar specialized drape is adapted for imaging devices such as a C-arm.

A subset of the control and display functions, generally shown at 34, are positioned at any location within the sterile field for surgical access.

To aid in calibration of the present invention, a phantom (not shown) is provided to verify performance. The phantom contains elements which represent Hounsfield densities typical of the central nervous system (CNS) and surrounding structures. Spatial, density and contrast resolution is then calibrated with the phantom positioned where the patient torso would rest by moving the CT system 10 in a scan position over the OR table extension 24.

Prior to each clinical case, a protocol is preferably followed, and an initialization protocol with setup and calibration phases should be followed. This protocol confirms that the CT system 10 and patient safety systems are functioning properly.

An exemplary protocol according to the present invention includes: If a CT guide is of the temporary configuration, it is secured at this time.

Thereafter, a CT compatible extension is secured to the end of the OR table. Proper placement is required in order to assure safe load bearing of a patient's weight. Moreover, the axis of a CT compatible table extension is essentially collinear with the axis of the remainder of the OR table in order to avoid potential collision between system components.

The CT compatible table extension includes an embedded or attached x-ray contrasting radiodensity shape to locate a scan image relative to a reference point. The opaque shape is constructed from a variety of conventional radio-opaque materials. The shape is alternatively a complex structure which allows identification based on the complexity of the shape or is well defined to allow calculation of a scan slice based on mathematical calculation.

Laser alignment devices are then secured to the radiolucent extension. The devices project illuminated alignment cues onto a target. The target or preferably a plurality of targets located at preselected intervals are positioned so as to assure a safe location of a patient with respect to a CT gantry.

A CT calibration phantom is then placed on the OR table in a position corresponding to the head and spine of the patient and a rigid patient protection shield is positioned thereover.

CT scans of the phantom are then collected. Phantom scans verify: the movement control system; the CT scan mechanism; and the CT spatial and density resolution.

Thereafter, the CT gantry is returned to the disengaged position, leaving the OR table freely and widely accessible for full clinical use.

Following a calibration procedure, a patient is positioned on the OR table. Routine clinical precautions for placement and padding are followed. Care is taken to position the anatomic region of CT interest within the allowable scanning locations of the radiolucent table extension.

Typically, physiologic monitoring lines and anesthetic airway management equipment are installed. All lines and tubing are then placed within the guideways of the radiolucent table extension and/or the table.

The laser alignment devices are then secured to the radiolucent table extension.

Reconfirmation of the proper alignment of the radiolucent extension allows for correction of any misalignment associated with the patient's weight or from the preceding positioning steps. Thereafter, no movement of the OR table volume encompassing the patient is performed.

The rigid patient protection shields are then secured to the OR table. Such shields can be repositioned both before and after sterile draping. Preferably, such shields are in position prior to moving the CT gantry.

Optionally, an initial scan is obtained prior to draping. This scan is useful, for example, in refining the planned surgical incision site.

The patient is then draped, and the shields are placed in the retracted position to allow the routine aspects of the clinical procedure to proceed in conventional fashion.

The CT gantry is then draped. Typically, standard perioperative precautions are followed with regards to respecting the sterility of the draped equipment. Draping of the CT is optionally postponed until the physician has decided that intra-operative scanning will be performed. Thereby saving the cost of the CT drape if scanning is not going to occur during a surgical procedure.

At the election of the operating physician, scans are performed during the surgical procedure. Prior to each of these intra-operative scans, the rigid protection shields are repositioned in the SCAN position and the laser alignment aids are used to reconfirm alignment of the radiolucent table extension. The CT gantry is optionally repositioned in a disengaged position while not in use to facilitate access to the patient.

Lastly, at the election of the operating physician, a final scan is performed at the conclusion of the surgical procedure. Clinical indications for so doing illustratively include documentation of the final anatomic result of the procedure. Prior to such a scan, the rigid protection shields are repositioned in the SCAN position and the laser alignment device is used to reconfirm current alignment of the radiolucent table extension. The CT system is optionally repositioned to the DISENGAGE position while not in use to facilitate access to the patient.

Various modifications of the instant invention in addition to those shown and described herein will be apparent to those skilled in the art from the above description. Such modifications are also intended to fall within the scope of the appended claims.

What is claimed is:

1. A surgical scanning system comprising:
   an operating room table having a long axis;
   a scanner supported on a carrier, said carrier movable relative to said operating room table;
   a guide adapted to engage said carrier, wherein said guide is collinear with the long axis of said operating room table;
   a stationary alignment target a measurable distance remote from said operating room table; and
   an alignment device and a target wherein one of said alignment device and said target is affixed to said operating room table and said alignment device projects a beam towards said target.

2. The system of claim 1 wherein said scanner is a computerized tomography scanner.

3. The system of claim 1 wherein said operating room table has an immovable table base.

4. The system of claim 1 wherein said carrier is selected from the group consisting of a pallet, platform and dolly.

5. The system of claim 1 wherein said operating room table engages said guide, said operating room table movable relative to said carrier.

6. The system of claim 1 wherein said operating room table is articulated.

7. The system of claim 1 wherein said operating table further comprises a radiolucent extension.

8. The system of claim 7 wherein the radiolucent extension comprises at least one marker of a contrasting radiodensity.

9. The system of claim 7 wherein said alignment device is affixed to the radiolucent extension.

10. The system of claim 1 further comprising a surgical drape adapted to engage said operating room table and a human body portion encompassing volume above said table.

11. The system of claim 10 wherein said surgical drape further comprises at least one fixturing fitting.

12. The system of claim 1 further comprising a scanner drape affixed over said scanner.

13. A surgical scanning system comprising:

an operating room table having a long axis;

a scanner supported on a carrier, said carrier movable relative to said operating room table; and a reference platform secured to a patient on said operating room table and defining a volume over said operating room table and retained in place during a scan.

14. The surgical scanning system of claim 13 further comprising a trajectory measurement device secured to said reference platform wherein said trajectory measuring device measures two angles between an axis of said scanner and said reference platform.

15. The system of claim 13 further comprising a stationary alignment target a measurable distance remote from said operating room table and an alignment device affixed to said operating room table.

16. The system of claim 13 wherein said scanner is a computerized tomography scanner.

17. The system of claim 13 wherein said operating room table has an immovable table base.

18. The system of claim 13 wherein said carrier is selected from the group consisting of a pallet, platform and dolly.

19. The system of claim 13 wherein said operating room table engages said guide, said operating room table movable relative to said carrier.

20. The system of claim 13 wherein said operating room table is articulated.

21. The system of claim 13 wherein said operating room table further comprises a radiolucent extension.

22. The system of claim 21 wherein the radiolucent extension comprises at least one marker of a contrasting radiodensity.

23. The system of claim 21 wherein said alignment device is affixed to the radiolucent extension.

24. The system of claim 13 further comprising a surgical drape adapted to engage said operating room table and a human body portion encompassing volume above said table.

25. The system of claim 24 wherein said surgical drape further comprises at least one fixturing fitting.

26. The system of claim 13 further comprising a scanner drape affixed over said scanner.

* * * * *